United States Patent
Rodrigues et al.

(10) Patent No.: US 12,048,571 B2
(45) Date of Patent: Jul. 30, 2024

(54) NEAR 2Pi COMPTON CAMERA FOR MEDICAL IMAGING

(71) Applicant: Siemens Medical Solutions USA, Inc., Malvern, PA (US)

(72) Inventors: Miesher Rodrigues, Buffalo Grove, IL (US); Ronald E. Malmin, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 752 days.

(21) Appl. No.: 17/250,439

(22) PCT Filed: Aug. 7, 2018

(86) PCT No.: PCT/US2018/045468
§ 371 (c)(1),
(2) Date: Jan. 21, 2021

(87) PCT Pub. No.: WO2020/032923
PCT Pub. Date: Feb. 13, 2020

(65) Prior Publication Data
US 2021/0282725 A1    Sep. 16, 2021

(51) Int. Cl.
*A61B 6/00* (2024.01)
*A61B 6/03* (2006.01)
(Continued)

(52) U.S. Cl.
CPC ............ *A61B 6/037* (2013.01); *A61B 6/0407* (2013.01); *A61B 6/4258* (2013.01);
(Continued)

(58) Field of Classification Search
CPC ............... A61B 6/0407; A61B 6/4258; A61B 6/4411; A61B 2562/18
See application file for complete search history.

(56) References Cited

U.S. PATENT DOCUMENTS

| | | |
|---|---|---|
| 4,529,882 A | 7/1985 | Lee |
| 4,700,074 A | 10/1987 | Bosnjakovic |

(Continued)

FOREIGN PATENT DOCUMENTS

| | | |
|---|---|---|
| CN | 102224434 | 10/2011 |
| CN | 107505647 | 12/2017 |

(Continued)

OTHER PUBLICATIONS

Ordonez, Caesar E., Alexander Bolozdynya, and Wei Chang. "Doppler broadening of energy spectra in Compton cameras." Nuclear Science Symposium, 1997. IEEE. vol. 2. IEEE, 1997.
(Continued)

*Primary Examiner* — Jason M Ip

(57) ABSTRACT

To capture more emitted photons with a Compton camera, the scatter detector is tilted (non-orthogonal angle) relative to a radial from the isocenter of the imaging system. The tilt creates a greater volume for scatter interaction. To capture more scatter photons, the catcher detector is non-planar, such as a multi-faced detector at least partially surrounding a volume behind the scatter detector. The tilted scatter detector alone, the non-planar catcher detector alone, or the tilted scatter detector and the non-planar catcher detector are used in the Compton camera.

17 Claims, 8 Drawing Sheets

(51) Int. Cl.
  *A61B 6/04* (2006.01)
  *A61B 6/42* (2024.01)
  *A61B 6/46* (2024.01)
  *G01T 1/164* (2006.01)
  *G01T 1/24* (2006.01)
  *G01T 1/29* (2006.01)

(52) U.S. Cl.
  CPC .......... *A61B 6/4411* (2013.01); *A61B 6/4452* (2013.01); *A61B 6/461* (2013.01); *G01T 1/1642* (2013.01); *G01T 1/242* (2013.01); *G01T 1/2985* (2013.01); *A61B 2562/18* (2013.01)

(56) References Cited

U.S. PATENT DOCUMENTS

| | | |
|---|---|---|
| 5,175,434 A | 12/1992 | Engdahl |
| 5,567,944 A | 10/1996 | Rohe et al. |
| 5,757,006 A | 5/1998 | DeVito et al. |
| 5,821,541 A | 10/1998 | Tumer |
| 6,323,492 B1 | 11/2001 | Clinthorne |
| 6,346,706 B1 | 2/2002 | Rogers et al. |
| 6,762,413 B2 | 7/2004 | Zeng |
| 6,791,090 B2 | 9/2004 | Lin et al. |
| 7,015,477 B2 | 3/2006 | Gunter |
| 7,045,789 B2 | 5/2006 | Ogawa et al. |
| 7,262,417 B2 | 8/2007 | Smith |
| 7,291,841 B2 | 11/2007 | Nelson et al. |
| 7,304,309 B2 | 12/2007 | Suhami |
| 7,321,122 B2 | 1/2008 | Bryman |
| 7,345,283 B2 | 3/2008 | Gunter |
| 7,504,635 B2 | 3/2009 | Ramsden |
| 7,550,738 B1 | 6/2009 | DeVito |
| 7,573,039 B2 | 8/2009 | Smith |
| 7,667,203 B2 | 2/2010 | Hindi et al. |
| 7,831,024 B2 | 11/2010 | Metzler et al. |
| 7,863,567 B1 | 1/2011 | Hynes et al. |
| 7,928,399 B2 | 4/2011 | Myjak et al. |
| 8,107,589 B2 | 1/2012 | Sakurai et al. |
| 8,153,986 B2 | 4/2012 | Mihailescu et al. |
| 8,217,362 B2 | 7/2012 | DeVito |
| 8,299,437 B2 | 10/2012 | Nakamura |
| 8,354,648 B2 | 1/2013 | Laurent et al. |
| 8,476,595 B2 | 7/2013 | McKinsey et al. |
| 8,515,011 B2 | 8/2013 | Mundy et al. |
| 8,519,343 B1 | 8/2013 | Mihailescu et al. |
| 8,716,669 B2 | 5/2014 | Miyaoka et al. |
| 8,742,360 B2 | 6/2014 | Yamaguchi et al. |
| 8,847,166 B2 | 9/2014 | Fukuchi et al. |
| 2002/0008205 A1 | 1/2002 | Kurfess et al. |
| 2002/0134942 A1 | 9/2002 | Pehl et al. |
| 2003/0161526 A1 | 8/2003 | Jupiter et al. |
| 2004/0021083 A1 | 2/2004 | Nelson et al. |
| 2004/0084624 A1 | 5/2004 | Meng et al. |
| 2005/0139775 A1 | 6/2005 | Gono et al. |
| 2005/0253073 A1 | 11/2005 | Joram et al. |
| 2007/0041490 A1 | 2/2007 | Jha et al. |
| 2007/0145281 A1 | 6/2007 | Ben-Haim et al. |
| 2007/0253530 A1 | 11/2007 | Mihailescu et al. |
| 2008/0088059 A1 | 4/2008 | Tang et al. |
| 2008/0139914 A1 | 6/2008 | Gaved et al. |
| 2008/0224061 A1 | 9/2008 | Smith |
| 2009/0202041 A1 | 8/2009 | Shirahata et al. |
| 2010/0090117 A1 | 4/2010 | Nelson |
| 2010/0294945 A1 | 11/2010 | Cussonneau |
| 2011/0198504 A1 | 8/2011 | Eigen |
| 2011/0303854 A1 | 12/2011 | DeVito |
| 2012/0043467 A1 | 2/2012 | Gueorguiev et al. |
| 2012/0132814 A1 | 5/2012 | Weinberg |
| 2012/0217386 A1 | 8/2012 | Ricci et al. |
| 2012/0290519 A1 | 11/2012 | Fontaine et al. |
| 2014/0110592 A1 | 4/2014 | Nelson et al. |
| 2015/0323685 A1 | 11/2015 | Nelson et al. |
| 2015/0331115 A1 | 11/2015 | Nelson et al. |
| 2017/0012308 A1 | 1/2017 | Ikeuchi |
| 2017/0261623 A1 | 9/2017 | Florido et al. |
| 2017/0311919 A1 | 11/2017 | Gagnon |
| 2018/0239036 A1 | 9/2018 | Ota et al. |
| 2019/0120978 A1* | 4/2019 | Hugg ..................... G01T 1/243 |

FOREIGN PATENT DOCUMENTS

| | | |
|---|---|---|
| CN | 108013888 | 5/2018 |
| EP | 2060932 B1 | 3/2017 |
| FR | 2354566 | 1/1978 |
| JP | 2004325405 | 11/2004 |
| JP | 2010101666 A | 5/2010 |
| JP | 2015197318 | 11/2015 |
| JP | 2016035437 | 3/2016 |
| WO | 2001088493 A1 | 11/2001 |
| WO | 2004010127 | 1/2004 |
| WO | 2017057674 A1 | 4/2017 |

OTHER PUBLICATIONS

International Search Report for Corresponding International Application No. PCT/US2018/045468.

* cited by examiner

FRONT-VIEW
BUMP-BONDED ASIC

FRONT-VIEW
FLEX-CABLE ASIC

NEAR 2Pi COMPTON CAMERA FOR MEDICAL IMAGING

BACKGROUND

The present embodiments relate to medical imaging using the Compton effect. The Compton effect allows for imaging higher energies than used for single photon emission computed tomography (SPECT). Compton imaging systems are constructed as test platforms, such as assembling a scatter layer and then a catcher layer mounted to a large framework. Electronics are connected to detect Compton-based events from emissions of a phantom. Compton imaging systems have failed to address design and constraint requirements for practical use in any commercial clinical settings. Current proposals lack the ability to be integrated into imaging platforms in the clinic or lack the design and constraint requirements (i.e., flexibility and scalability) to address commercial and diagnostic needs.

Compton-cameras may have low sensitivity ($) and poor image quality (IQ). The absolute number of scattered photons in the scatter layer is low due to the geometry (e.g., source-scatter solid angle $\Omega \ll 4\pi$), material (e.g., low scatter fraction in the detection material which favors photoelectric effect), and detector fabrication limitations (e.g., practical detector thickness that can be manufactured for both scatter and catcher layers is bounded, such as a maximum of ~1 mm for Si detectors and 2 mm ... 10 mm for CZT detectors). The number of caught scattered photons in the catcher layer is low due to geometry (e.g., scatter-catcher solid angle $\Omega \ll 4\pi$). Doppler broadening degrades image quality of Compton cameras. The contribution of Doppler broadening to the Compton angle uncertainty depends on incident photon energy $E_0$, scattered angle $\theta$, and the energy of moving electrons bound to the target atom. Limited detector energy resolution causes additional Compton angle uncertainties. Limited detector position resolution in both scatter and catcher layers causes additional Compton cone annular offsets.

SUMMARY

By way of introduction, the preferred embodiments described below include methods and systems for medical imaging. To capture more emitted photons with a Compton camera, the scatter detector is tilted (non-orthogonal angle) relative to a radial from the isocenter of the imaging system. The tilt creates a greater volume for scatter interaction. To capture more scatter photons, the catcher detector is non-planar, such as a multi-faced detector at least partially surrounding a volume behind the scatter detector. The tilted scatter detector alone, the non-planar catcher detector alone, or the tilted scatter detector and the non-planar catcher detector are used in the Compton camera.

In a first aspect, a Compton camera is provided for medical imaging. A bed is for a patient space having an iso center axis. A first module has a first scatter detector and a first catcher detector spaced from the first scatter detector. The first scatter detector has an outer surface facing the iso center axis where the outer surface is away from orthogonal by an angle of at least 20 degrees to a radial line extending perpendicular from the iso center axis through a center of the first scatter detector. The first catcher detector forms a substantially semi-spherical surround behind the first scatter detector relative to the patient space. An image processor is configured to determine angles of incidence for Compton events from the first scatter detector and the first catcher detector.

In a second aspect, a medical imaging system includes a Compton camera with a scatter detector arranged to receive emissions from a patient. The scatter detector has an outer surface facing the patient where the outer surface is away from orthogonal by an angle of at least 20 degrees to a radial line extending perpendicular from a longitudinal axis of the patient through the scatter detector.

In a third aspect, a medical imaging system includes a Compton camera with a scatter detector and a catcher detector. The scatter detector is arranged to receive emissions from a patient. The catcher detector is arranged to receive scatter from the scatter detector due to the emissions from a patient. The catcher detector includes a multi-sided detection surface positioned behind the scatter detector relative to the patient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
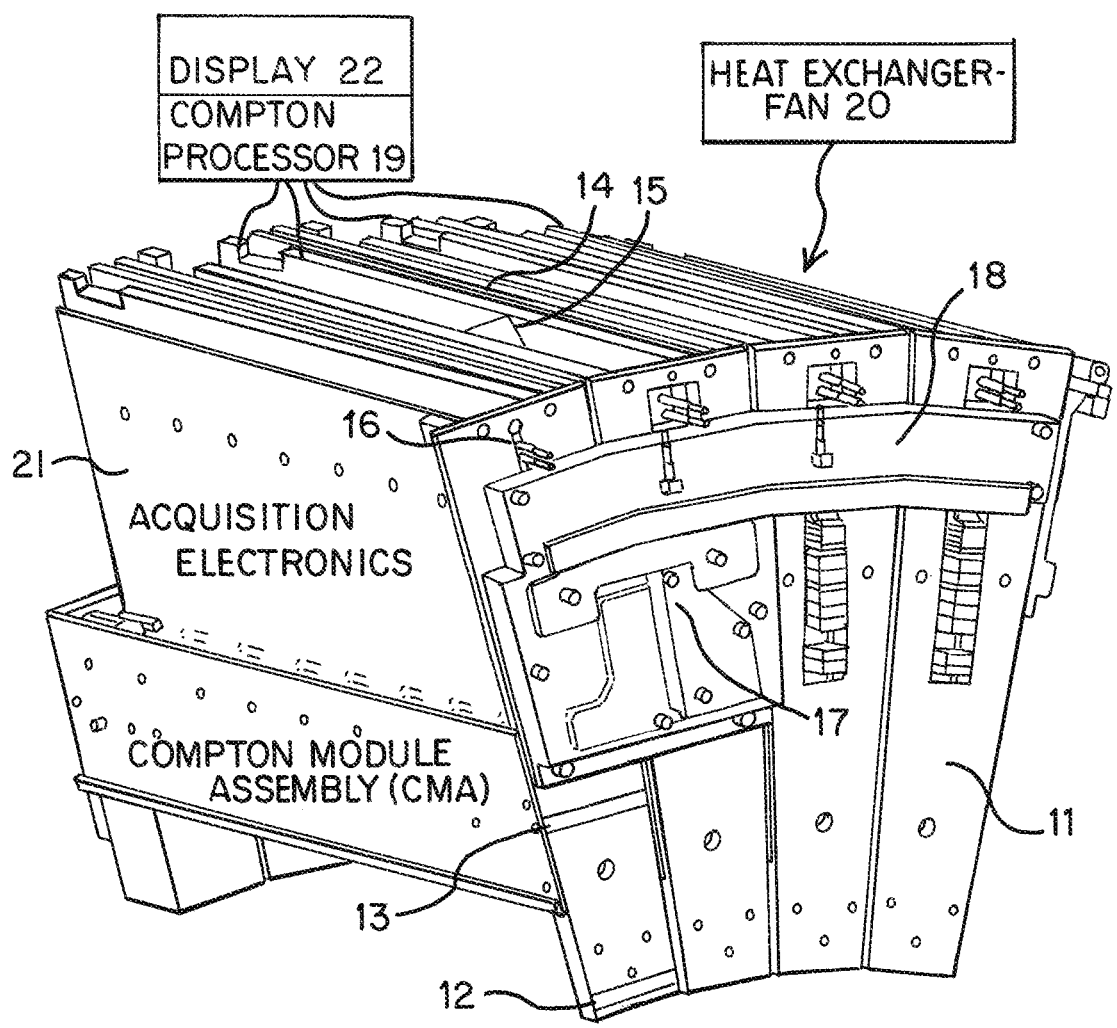
FIG. 1 is perspective view of multiple modules of a Compton camera according to one embodiment.

FIGS. 1-9 are directed to a multi-modality compatible Compton camera. A modular design is used to form the Compton camera for use with various other imaging modalities. FIGS. 11-15 are directed to a Compton camera with a tilted scatter detector and/or near $2\pi$ catcher detector. The titled scatter detector and/or near $2\pi$ catcher detector are used in modules of FIGS. 1-9, other modules, or without modules. After a summary of the tilted scatter detector and/or $2\pi$ catcher detector embodiments, the Compton camera of FIGS. 1-9 is described. Many of the features and components of the Compton camera of FIGS. 1-9 may be used in the tilted scatter detector and/or near $2\pi$ catcher detector embodiments later described for FIGS. 11-15.

A more efficient Compton camera is provided by the tilted scatter detector and/or near $2\pi$ catcher detector. Sensitivity ($) and/or image quality (IQ) may be improved. Synchronization and triggering limitations between modules may be avoided by capturing photons at higher rates within a module. Tilting the scatter detector and/or using a near $2\pi$ catcher detector may improve the sensitivity ($) as compared to the parallel plate scatter and catcher detectors of FIG. 1 by ~15 times. The absolute number of scattered photons may be increased by ~3-5 times using the tilted scatter detector, and the number of caught photons may be increased by ~3-5 times using the near $2\pi$ catcher detector.

The tilted scatter detector and/or near $2\pi$ catcher detector may be applied to any Compton-Camera regardless of the detection materials used, readout electronics and/or size of imaging object. The design configuration of each module may be re-arranged and optimized for different imaging tasks, assuming a quantized number of different modules that may be swapped in the system for different tasks during design. Using modularized smaller Compton-cameras forming a larger imaging system, with reduced or near zero cross-talk between modules due to shielding, a lower requirement for electronics (e.g., ASIC/FPGA) cross-talk and inter-module triggers at high rates results.

Referring to FIGS. 1-9, a medical imaging system includes a multi-modality compatible Compton camera with segmented detection modules. The Compton camera, such as a Compton camera ring, is segmented into modules that house the detection units. Each module is independent, and when assembled into a ring or partial ring, the modules may communicate with each other. The modules are independent yet can be assembled into a multi-module unit that produces Compton scattering-based images. Cylindrically symmetric modules or spherical shell segmented modules may be used.

The scatter-catcher pair, modular arrangement allows efficient manufacturing, is serviceable in the field, and is cost and energy efficient. The modules allow for the design freedom to change the radius for each radial detection unit, angular span of one module, and/or axial span. The scatter-catcher pair modules are multi-modality compatible and/or form a modular ring Compton camera for clinical emission imaging. This design allows flexibility, so the Compton camera may be added to existing computed tomography (CT), magnetic resonance (MR), positron emission tomography (PET) or other medical imaging platforms, either as axially separated systems or as fully integrated systems. Each module may address heat dissipation, data collection, calibration, and/or allow for efficient assembly as well as servicing.

Each scatter-catcher paired module is formed from commercially suitable solid-state detector modules (e.g., Si, CZT, CdTe, HPGe or similar), allowing for an energy range of 100-3000 keV. Compton imaging may be provided with a wider range of isotope energies (>2 MeV), enabling new tracers/markers through selection of the scatter-catcher detectors. The modularity allows for individual module removal or replacement, allowing for time and cost-efficient service. The modules may be operated independently and isolated or may be linked for cross-talk, allowing for improved image quality and higher efficiency in detecting Compton events using a scatter detector of one module and a catcher detector of another module.

The modularity allows for flexible design geometry optimized to individual requirements, such as using a partial ring for integration with a CT system (e.g., connected between the x-ray source and detector), a few modules (e.g., tiling) used for integration with a single photon emission computed tomography gamma camera or other space limited imaging system, or a full ring. Functional imaging based on Compton-detected events may be added to other imaging systems (e.g., CT, MR, or PET). Multiple full or partial rings may be placed adjacent to each other for greater axial coverage of the Compton camera. A dedicated or stand-alone Compton-based imaging system may be formed. In one embodiment, the modules include a collimator for lower energies (e.g., <300 keV), providing for multichannel and multiplexed imaging (e.g., high energies using the scatter-catcher detectors for Compton events and low energies using one of the detectors for SPECT or PET imaging). The modules may be stationary or fast rotating (0.1 rpm<<ω<<240 rpm). The dimensional, installation, service, and/or cost constraints are addressed by the scatter-catcher paired modules.

FIG. 1 shows one embodiment of modules 11 for a Compton camera. Four modules 11 are shown, but additional or fewer modules may be used. The Compton camera is formed from one or more modules, depending on the desired design of the Compton camera.

The Compton camera is for medical imaging. A space for a patient relative to the modules is provided so that the modules are positioned to detect photons emitted from the patient. A radiopharmaceutical in the patient includes a radio-isotope. A photon is emitted from the patient due to decay from the radio-isotope. The energy from the radio-isotope may be 100-3000 keV, depending on the material and structure of the detectors. Any of various radio-isotopes may be used for imaging a patient. Modules 11 optimized for different isotopes may be interleaved to cover any range (e.g., the entire) of energy spectrum. For example, a $1^{st}$ module for 100-400 keV, a second module for 300-600 keV, a third module for 500-above, a 4th module for 100-400 keV, ... covering the entire full ring and/or partially populating the ring.

Each of the modules 11 includes the same or many of the same components. A scatter detector 12, a catcher detector 13, circuit boards 14, and baffle 15 are provided in a same housing 21. Additional, different, or fewer components may be provided. For example, the scatter detector 12 and catcher detector 13 are provided in the housing 21 without other components. As another example, a fiber optic data line 16 is provided in all or a sub-set of the modules 11.

The modules 11 are shaped for being stacked together. The modules 11 mate with each other, such as having matching indentation and extensions, latches, tongue-and-grooves, or clips. In other embodiments, flat or other surfaces are provided for resting against each other or a divider. Latches, clips, bolts, tongue-and-groove or other attachment mechanisms for attaching a module 11 to any adjacent modules 11 are provided. In other embodiments, the module 11 attaches to a gantry or other framework with or without direct connection to any adjacent modules 11.

The connection or connections to the other modules 11 or gantry may be releasable. The module 11 is connected and may be disconnected. The connection may be releasable, allowing removal of one module 11 or a group of modules 11 without removing all modules 11.

For forming a Compton camera from more than one module 11, the housing 21 and/or outer shape of the modules 11 is wedge shaped. The modules 11 may be stacked around an axis to form a ring or partial ring due to the wedge shape. The part closer to the axis has a width size that is narrower along a dimension perpendicular to the axis than a width size of a part further from the axis. In the modules 11 of FIG. 1, the housings 21 have the widest part furthest from the axis. In other embodiments, the widest part is closer to the axis but spaced away from the narrowest part closest to the axis. In the wedge shape, the scatter detector 12 is nearer to the narrower part of the wedge shape than the catcher detector 13. This wedge shape in cross-section along a plane normal to the axis allows stacking of the modules 11 in abutting positions, adjacently, and/or connected to form at least part of a ring about the axis.

The taper of the wedge provides for a number N of modules 11 to form a complete ring around the axis. Any number N may be used, such as N=10-30 modules. The number N may be configurable, such as using different housings 21 for different numbers N. The number of modules 11 used for a given Compton camera may vary, depending on the design of the Compton camera (e.g., partial ring). The wedge shape may be provided along other dimensions, such as having a wedge shape in a cross-section parallel to the axis.

The modules 11 as stacked are cylindrically symmetric as connected with a gantry of a medical imaging system. A narrowest end of the wedged cross-section is closest to a patient space of the medical imaging system and a widest end of the wedged cross-section may be furthest from the patient space. In alternative embodiments, other shapes than wedge allowing for stacking together to provide a ring or generally curved shape of the stack may be provided.

The housing 21 is metal, plastic, fiberglass, carbon (e.g., carbon fiber), and/or other material. In one embodiment, different parts of the housing 21 are of different materials. For example, tin is used for the housing around the circuit boards 14. Aluminum is used to hold the scatter detector 12 and/or catcher detector 13. In another example, the housing 12 is of the same material, such as aluminum.

The housing 21 may be formed from different structures, such as end plates having the wedge shape, sheets of ground plane housing the circuit boards 14, and separate structure for walls holding the scatter detector 12 and catcher detector 13 where the separate structure is formed of material through which photons of a desired energy from a Compton event may pass (e.g., aluminum or carbon fiber). In alternative embodiments, walls are not provided for the modules 11 between the end plates for a region where the scatter detector 12 and/or catcher detector 13 are positioned, avoiding interference of photons passing from the scatter detector 12 of one module 11 to a catcher detector 13 of another module 11. The housing 21 by and/or for holding the detectors 12, 13 is made of low attenuating material, such as aluminum or carbon fiber.

The housing 21 may seal the module or includes openings. For example, openings for air flow are provided, such as at a top of widest portion of the wedge shape at the circuit boards 14. The housing 21 may include holes, grooves, tongues, latches, clips, stand-offs, bumpers, or other structures for mounting, mating, and/or stacking.

Each of the solid-state detector modules 11 includes both scatter and catcher detectors 12, 13 of a Compton sensor. By stacking each module, the size of the Compton sensor is increased. A given module 11 itself may be a Compton sensor since both the scatter detector 12 and catcher detector 13 are included in the module.

The modules 11 may be separately removed and/or added to the Compton sensor. For a given module 11, the scatter detector 12 and/or catcher detector 13 may be removable from the module 11. For example, a module 11 is removed for service. A faulty one or both detectors 12, 13 are removed from the module 11 for replacement. Once replaced, the refurbished module 11 is placed back in the medical imaging system. Bolts, clips, latches, tongue-and-groove, or other releasable connectors may connect the detectors 12, 13 or part of the housing 21 for the detectors 12, 13 to the rest of the module 11.

Figure 2:
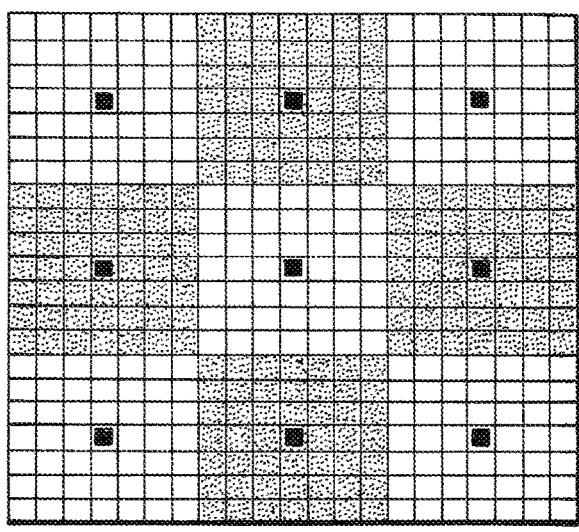
FIG. 2 illustrates an example scatter detector.

The scatter detector 12 is a solid-state detector. Any material may be used, such as Si, CZT, CdTe, HPGe, and/or other material. The scatter detector 12 is created with wafer fabrication at any thickness, such as about 4 mm for CZT. Any size may be used, such as about 5×5 cm. FIG. 2 shows a square shape for the scatter detector 12. Other shapes than square may be used, such as rectangular. For the modules 11 of FIG. 1, the scatter detector 12 may be rectangular extending between two wedge-shaped end-plates.

In the module 11, the scatter detector 12 has any extent. For example, the scatter detector 12 extends from one wedge-shaped end wall to the other wedge-shaped end wall. Lesser or greater extent may be provided, such as extending between mountings within the module 11 or extending axially beyond one or both end-walls. In one embodiment, the scatter detector 12 is at, on, or by one end wall without extended to another end wall.

The scatter detector 12 forms an array of sensors. For example, the 5×5 cm scatter detector 12 of FIG. 2 is a 21×21 pixel array with a pixel pitch of about 2.2 mm. Other numbers of pixels, pixel pitch, and/or size of arrays may be used.

The scatter detector 12 includes semiconductor formatted for processing. For example, the scatter detector 12 includes an application specific integrated circuit (ASIC) for sensing photon interaction with an electron in the scatter detector 12. The ASIC is collocated with the pixels of the scatter detector 12. The ASIC is of any thickness. A plurality of ASICs may be provided, such as 9 ASICS in a 3×3 grid of the scatter detector 12.

The scatter detector 12 may operate at any count rate, such as >100 kcps/mm. Electricity is generated by a pixel due to the interaction. This electricity is sensed by the application specific integrated circuit. The location, time, and/or energy is sensed. The sensed signal may be conditioned, such as amplified, and sent to one or more of the circuit boards 14. A flexible circuit, wires, or other communications path carries the signals from the ASIC to the circuit board 14.

Compton sensing operates without collimation. Instead, a fixed relationship between energy, position, and angle of a photon interaction at the scatter detector 12 relative to a photon interaction at the catcher detector 13 is used to determine the angle of the photon entering the scatter detector 12. A Compton process is applied using the scatter detector 12 and the catcher detector 13.

Figure 3:
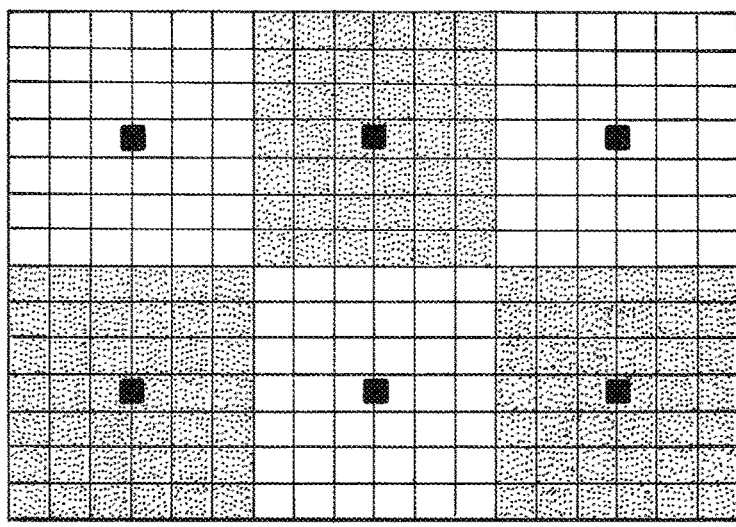
FIG. 3 illustrates an example catcher detector.

The catcher detector 13 is a solid-state detector. Any material may be used, such as Si, CZT, CdTe, HPGe, and/or other material. The catcher detector 13 is created with wafer fabrication at any thickness, such as about 10 mm for CZT. Any size may be used, such as about 5×5 cm. The size may be larger along at least one dimension than the scatter detector 12 due to the wedge shape and spaced apart positions of the scatter detector 12 and the catcher detector 13. FIG. 3 shows a rectangular shape for the catcher detector 13 but other shapes may be used. For the modules 11 of FIG. 1, the catcher detector 13 may be rectangular extending between two end-plates where the length is the same as and the width is greater than the scatter detector 12.

The catcher detector 12 forms an array of sensors. For example, the 5×6 cm catcher detector 13 of FIG. 3 is a 14×18 pixel array with a pixel pitch of about 3.4 mm. The pixel size is larger than the pixel size of the scatter detector 12. The number of pixels is less than the number of pixels of the scatter detector 12. Other numbers of pixels, pixel pitch, and/or size of arrays may be used. Other relative pixels sizes and/or numbers of pixels may be used.

In the module 11, the catcher detector 13 has any extent. For example, the catcher detector 13 extends from one wedge-shaped end wall to the other wedge-shaped end wall. Lesser or greater extent may be provided, such as extending between mountings within the module 11 or extending axially beyond one or both end-walls. In one embodiment, the catcher detector 13 is at, on, or by one end wall without extending to another end wall.

The catcher detector 13 includes semiconductor formatted for processing. For example, the catcher detector 13 includes an ASIC for sensing photon interaction with an electron in the catcher detector 13. The ASIC is collocated with the pixels of the catcher detector 13. The ASIC is of any thickness. A plurality of ASICS may be provided, such as 6 ASICS in a 2×3 grid of the catcher detector 13.

The catcher detector 13 may operate at any count rate, such as >100 kcps/mm. Electricity is generated by a pixel due to the interaction. This electricity is sensed by the ASIC. The location, time, and/or energy is sensed. The sensed signal may be conditioned, such as amplified, and sent to one or more of the circuit boards 14. A flexible circuit, wires, or other communications path carries the signals from the ASIC to the circuit board 14.

The catcher detector 13 is spaced from the scatter detector 12 by any distance along a radial line from the axis or normal to the parallel scatter and catcher detectors 12, 13. In one embodiment, the separation is about 20 cm, but greater or lesser separation may be provided. The space between the catcher detector 13 and the scatter detector 12 is filled with air, other gas, and/or other material with low attenuation for photons at the desired energies.

The circuit boards 14 are printed circuit boards, but flexible circuits or other materials may be used. Any number of circuit boards 14 for each module may be used. For example, one circuit board 14 is provided for the scatter detector 12 and another circuit board 14 is provided for the catcher detector 13.

The circuit boards 14 are within the housing 21 but may extend beyond the housing 21. The housing 21 may be grounded, acting as a ground plane for the circuit boards 14. The circuit boards 14 are mounted in parallel with each other or are non-parallel, such as spreading apart in accordance with the wedge shape. The circuit boards are positioned generally orthogonal to the catcher detector 13. Generally is used to account for any spread due to the wedge shape. Brackets, bolts, screws, and/or stand-offs from each other and/or the housing 21 are used to hold the circuit boards 14 in place.

The circuit boards 14 connect to the ASICS of the scatter and catcher detectors 12, 13 through flexible circuits or wires. The ASICs output detected signals. The circuit boards 14 are acquisition electronics, which process the detected signals to provide parameters to the Compton processor 19. Any parameterization of the detected signals may be used. In one embodiment, the energy, arrival time, and position in three-dimensions is output. Other acquisition processing may be provided.

The circuit boards 14 output to each other, such as through a galvanic connection within a module 11, to the data bridge 17, and/or to a fiber optic data link 16. The fiber data link 16 is a fiber optic interface for converting electrical signals to optical signals. A fiber optic cable or cables provide the acquisition parameters for events detected by the scatter and catcher detectors 12, 13 to the Compton processor 19.

The data bridge 17 is a circuit board, wires, flexible circuit, and/or other material for galvanic connection to allow communications between modules 11. A housing or protective plate may cover the data bridge 17. The data bridge 17 releasably connects to one or more modules 11. For example, plugs or mated connectors of the data bridge 17 mate with corresponding plugs or mated connectors on the housing 21 and/or circuit boards 14. A latch, clip, tongue-and-groove, screw, and/or bolt connection may be used to releasably hold the data bridge 17 in place with the modules 11.

The data bridge 17 allows communications between the modules. For example, the fiber data link 16 is provided in one module 11 and not another module 11. The cost of a fiber data link 16 in every module 11 is avoided. Instead, the parameters output by the other module 11 are provided via the data bridge 17 to the module 11 with the fiber data link 16. The circuit board or boards 14 of the module 11 with the fiber data link 16 route the parameter output to the fiber data link 16, using the fiber data link 16 to report detected events from more than one module 11. In alternative embodiments, each module 11 includes a fiber data link 16, so the data bridge 17 is not provided or communicates other information.

The data bridge 17 may connect other signals between the modules 11. For example, the data bridge 17 includes a conductor for power. Alternatively, a different bridge provides power to the modules 11 or the modules 11 are individually powered. As another example, clock and/or synchronization signals are communicated between modules 11 using the data bridge 17.

In the embodiment of FIG. 1, a separate clock and/or synchronization bridge 18 is provided. The clock and/or synchronization bridge 18 is a circuit board, wires, flexible circuit, and/or other material for galvanic connection to allow communication of clock and/or synchronization signals between modules 11. A housing or protective plate may cover the clock and/or synchronization bridge 18. The clock and/or synchronization bridge 18 releasably connects to one or more modules 11. For example, plugs or mated connectors of the clock and/or synchronization bridge 18 mate with corresponding plugs or mated connectors on the housing 21 and/or circuit boards 14. A latch, clip, tongue-and-groove, screw, and/or bolt connection may be used to releasably hold the clock and/or synchronization bridge 18 in place with the modules 11.

The clock and/or synchronization bridge 18 may connect with the same or different grouping of modules 11 as the data bridge 17. In the embodiment shown in FIG. 1, the data bridge 17 connects between pairs of modules 11 and the clock and/or synchronization bridge 18 connects over groups of four modules 11.

The clock and/or synchronization bridge 18 provides a common clock signal and/or synchronization signals for synchronizing clocks of the modules 11. One of the parameters formed by the circuit boards 14 of each module 11 is the time of detection of the event. Compton detection relies on pairs of events—a scatter event and a catcher event. Timing is used to pair events from the different detectors 12, 13. The common clocking and/or synchronization allows for accurate pairing where the pair of events are detected in different modules 11. In alternative embodiments, only scatter and catcher events detected in a same module 11 are used, so the clock and/or synchronization bridge 18 may not be provided.

Other links or bridges between different modules 11 may be provided. Since the bridges 17, 18 are removable, individual modules 11 may be removed for service while leaving remaining modules 11 in the gantry.

Each module 11 is air cooled. Holes may be provided for forcing air through the module 11 (i.e., entry and exit holes). One or more baffles 15 may be provided to guide the air within the module 11. Water, conductive transfer, and/or other cooling may be alternatively or additionally provided.

In one embodiment, the top portion of the wedge-shape module 11 or housing 21 is open (i.e., no cover on the side furthest from the patient area). One or more baffles 15 are provided along the centers of one or more circuit boards 14 and/or the housing 21. A fan and heat exchanger 20 force cooled or ambient temperature air into each module 11, such as along one half of the module 11 at a location spaced away from the catcher detector 13 (e.g., top of the module 11). The baffles 15 and/or circuit boards 14 guide at least some of the air to the airspace between the scatter detector 12 and the catcher detector 13. The air then passes by the baffles 15 and/or circuit boards 14 on another part (e.g., another half) of the module 11 for exiting to the heat exchanger 20. Other routing of the air may be provided.

The heat exchanger and fan 20 is provided for each individual module 11, so may be entirely or partly within the module 11. In other embodiments, ducting, baffles, or other structure route air to multiple modules 11. For example, groups of four modules 11 share a common heat exchanger and fan 20, which is mounted to the gantry or other framework for cooling the group of modules 11.

For forming a Compton sensor, one or more modules 11 are used. For example, two or more modules 11 are positioned relative to a patient bed or imaging space to detect photon emissions from the patient. An arrangement of a greater number of modules 11 may allow for detection of a greater number of emissions. By using the wedge shape, modules 11 may be positioned against, adjacent, and/or connected with each other to form an arc about the patient space. The arc may have any extent. The modules 11 directly contact each other or contact through spacers or the gantry with small separation (e.g., 10 cm or less) between the modules 11.

In one example, four modules 11 are positioned together, sharing a clock and/or synchronization bridge 18, one or more data bridges 17, and a heat exchanger and fan 20. One, two, or four fiber data links 16 are provided for the group of modules 11. Multiple such groups of modules 11 may be positioned apart or adjacent to each other for a same patient space.

Due to the modular approach, any number of modules 11 may be used. Manufacturing is more efficient and costly by building multiple of the same component despite use of any given module 11 in a different arrangement than used for others of the modules 11.

The fiber data links 16 of the modules 11 or groups of modules 11 connect to the Compton processor 19. The Compton processor 19 receives the values for the parameters for the different events. Using the energy and timing parameters, scatter and catcher events are paired. For each pair, the spatial locations and energies of the pair of events are used to find the angle of incidence of the photon on the scatter detector 12. The event pairs are limited to events in the same module 11 in one embodiment. In another embodiment, catcher events from the same or different modules 11 may be paired with scatter events from a given module 11. More than one Compton processor 19 may be used, such as for pairing events from different parts of a partial ring 40.

Once paired events are linked, the Compton processor 19 or another processor may perform computed tomography to reconstruct a distribution in two or three dimensions of the detected emissions. The angle or line of incidence for each event is used in the reconstruction. The reconstructed distribution of emissions is used to generate a Compton image.

The display 22 is a CRT, LCD, projector, printer, or other display. The display 22 is configured to display the Compton image. The image or images are stored in a display plane buffer and read out to the display 22. The images may be displayed separately or are combined, such as displaying the Compton image overlaid with or adjacent to a SPECT image.

Figure 4A:
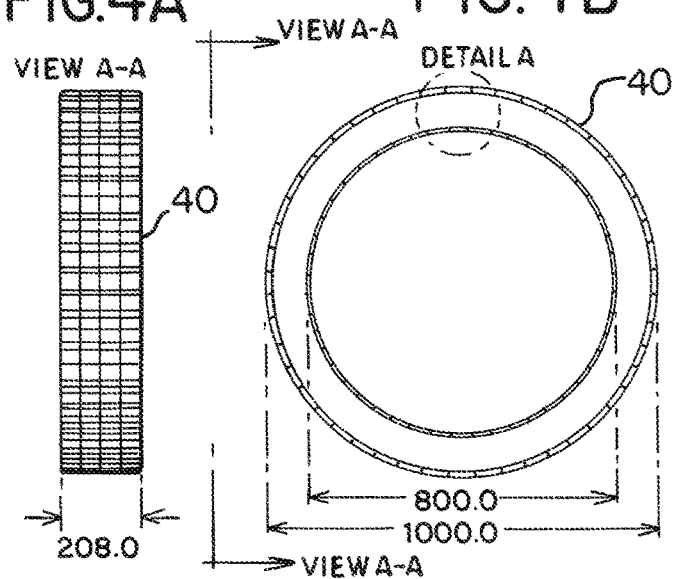
FIG. 4A is a side view of one embodiment of a Compton camera.
Figure 4B:
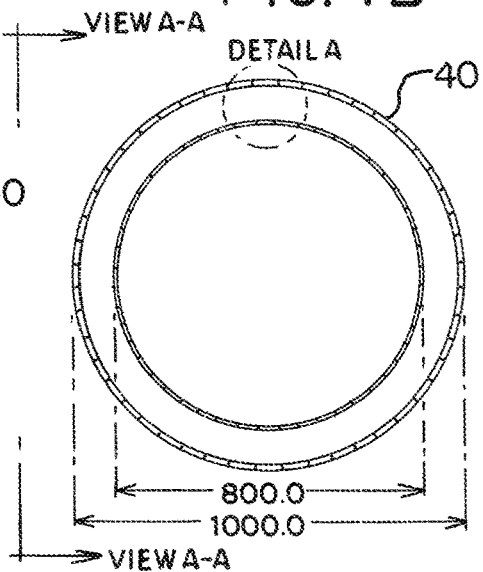
FIG. 4B is an end view of the Compton camera of FIG. 4A.
Figure 4C:
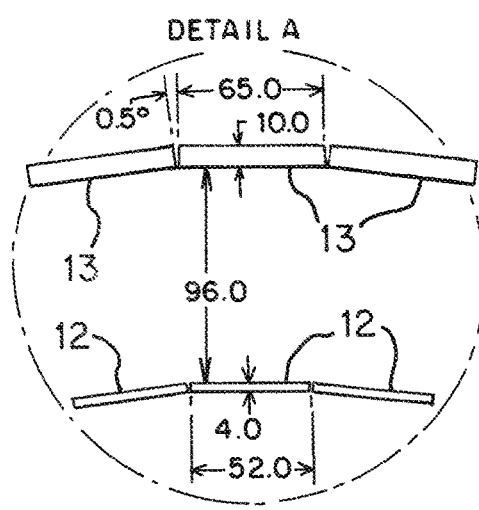
FIG. 4C is a detail view of a part of the Compton camera of FIG. 4B.
Figure 5:
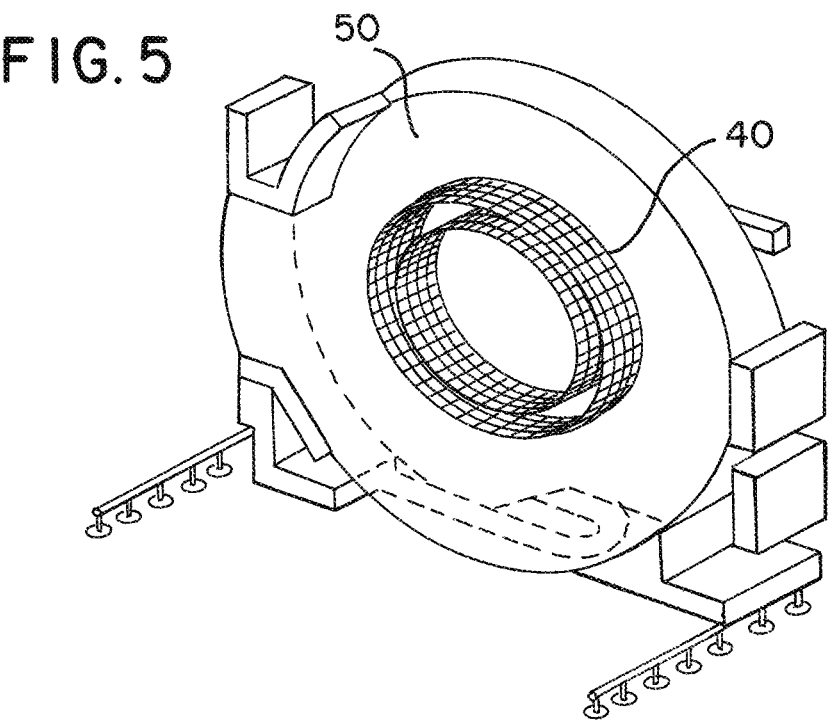
FIG. 5 is a perspective view of one embodiment of a Compton camera in a medical imaging system.
Figure 6:
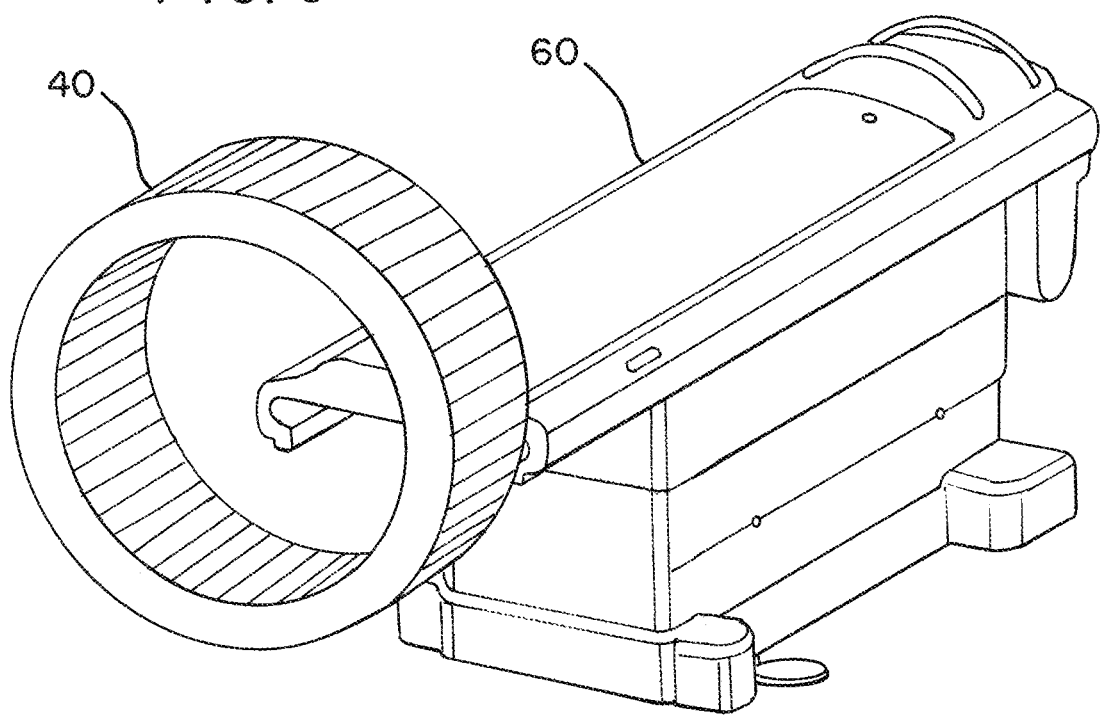
FIG. 6 is a perspective view of one embodiment of a full-ring Compton camera in a medical imaging system.

FIGS. 4A-6 shows one example arrangement of modules 11. The modules 11 form a ring 40 surrounding a patient space. FIG. 4A shows four such rings 40 stacked axially. FIG. 4B shows the scatter detectors 12 and corresponding catcher detectors 13 of the modules 11 in the ring 40. FIG. 4C shows a detail of a part of the ring 40. Three modules 11 provide corresponding pairs of scatter and catcher detectors 12, 13. Other dimensions than shown may be used. Any number of modules 11 may be used to form the ring 40. The ring 40 completely surrounds the patient space, but gaps with less than ½ module width may be provided. Within a housing of a medical imaging system, the ring 40 connects with a gantry 50 or another framework as shown in FIG. 5. The ring 40 may be positioned to allow a patient bed 60 to move a patient into and/or through the ring 40. FIG. 6 shows an example of this configuration.

Figure 7:
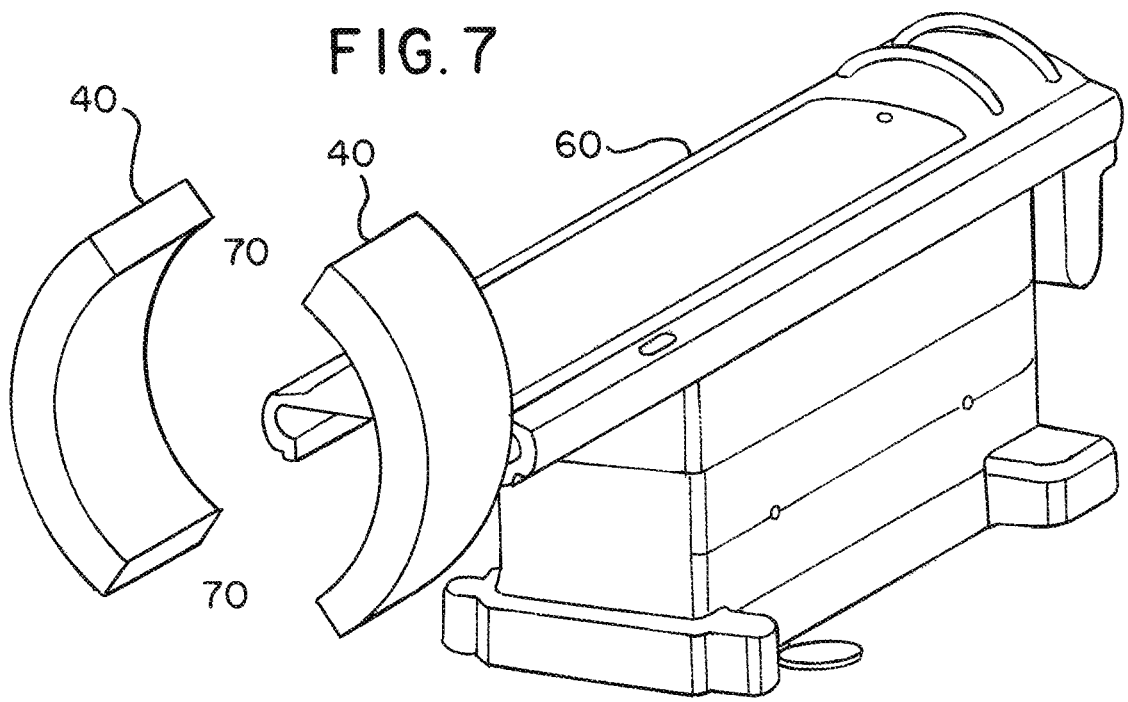
FIG. 7 is a perspective view of one embodiment of a partial-ring Compton camera in a medical imaging system.

The ring may be used for Compton-based imaging of emissions from a patient. FIG. 7 shows an example of using the same type of modules 11 but in a different configuration. A partial ring 40 is formed. One or more gaps 70 are provided in the ring 40. This may allow for other components to be used in the gaps and/or to make a less costly system by using fewer modules 11.

Figure 8:
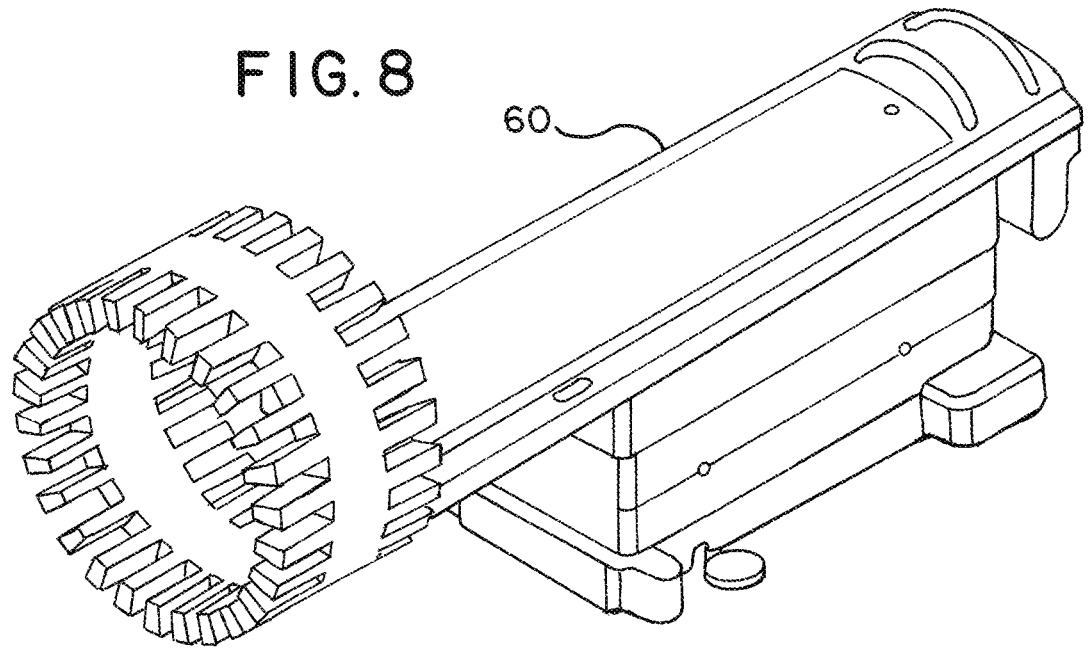
FIG. 8 is a perspective view of one embodiment of a full-ring Compton camera with partial-rings in axial extension in a medical imaging system.

FIG. 8 shows another configuration of modules 11. The ring 40 is a full ring. Additional partial rings 80 are stacked axially relative to the bed 60 or patient space, extending the axial extent of detected emissions. The partial rings 80 are in an every other or every group of N modules 11 (e.g., N=4) distribution rather than the two gaps 70 partial ring 40 of FIG. 7. The additional rings may be full rings. The full ring 40 may be a partial ring 80. The different rings 40 and/or partial rings 80 are stacked axially with no or little (e.g., less than ½ a module's 11 axial extent) apart. Wider spacing may be provided, such as having a gap of more than one module's 11 axial extent.

Figure 9:
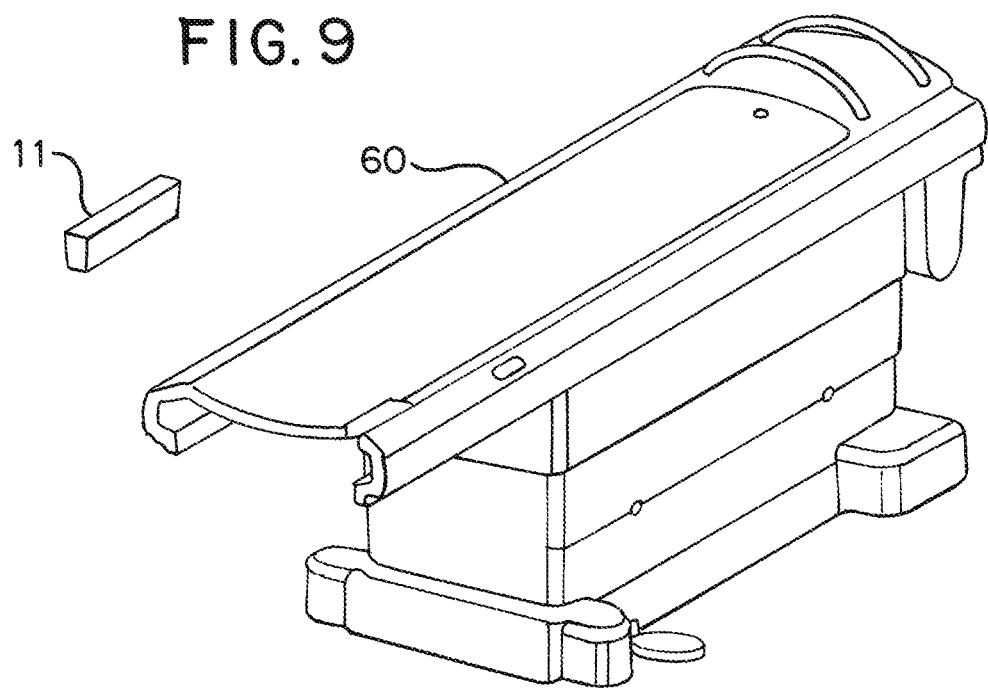
FIG. 9 is a perspective view of one embodiment of a single module-based Compton camera in a medical imaging system.

FIG. 9 shows yet another configuration of modules 11. One module 11 or a single group of modules 11 is positioned by the patient space or bed 60. Multiple spaced apart single modules 11 or groups (e.g., group of four) may be provided at different locations relative to the bed 60 and/or patient space.

In any of the configurations, the modules 11 are held in position by attachment to a gantry, gantries, and/or other framework. The hold is releasable, such as using bolts or screws. The desired number of modules 11 are used to assemble the desired configuration for a given medical imaging system. The gathered modules 11 are mounted in the medical imaging system, defining or relative to the patient space. The result is a Compton sensor for imaging the patient.

The bed 60 may move the patient to scan different parts of the patient at different times. Alternatively or additionally, the gantry 50 moves the modules 11 forming the Compton sensor. The gantry 50 translates axially along the patient space and/or rotates the Compton sensor around the patient space (i.e., rotating about the long axis of the bed 60 and/or patient). Other rotations and/or translations may be provided, such as rotating the modules 11 about an axis non-parallel to the long axis of the bed 60 or patient. Combinations of different translations and/or rotations may be provided.

The medical imaging system with the Compton sensor is used as a stand alone imaging system. Compton sensing is used to measure distribution of radiopharmaceutical in the patient. For example, the full ring 40, partial ring 40, and/or axially stacked rings 40, 80 are used as a Compton-based imaging system.

In other embodiments, the medical imaging system is a multi-modality imaging system. The Compton sensor formed by the modules 11 is one modality, and another modality is also provided. For example, the other modality is a single photon emission computed tomography (SPECT), a PET, a CT, or a MR imaging system. The full ring 40, partial ring 40, axially stacked rings 40,80, and/or singular module 11 or group of modules 11 are combined with the sensors for the other type of medical imaging. The Compton sensor may share a bed 60 with the other modality, such as being positioned along a long axis of the bed 60 where the bed positions the patient in the Compton sensor in one direction and in the other modality in the other direction.

The Compton sensor may share an outer housing with the other modality. For example, the full ring 40, partial ring 40, axially stacked rings 40,80, and/or singular module 11 or group of modules 11 are arranged within a same imaging system housing for the sensor or sensors of the other modality. The bed 60 positions the patient within the imaging system housing relative to the desired sensor. The Compton sensor may be positioned adjacent to the other sensors axially and/or in a gap at a same axial location. In one embodiment, the partial ring 40 is used in a computed tomography system. The gantry holding the x-ray source and the x-ray detector also holds the modules 11 of the partial ring 40. The x-ray source is in one gap 70, and the detector is in another gap 70. In another embodiment, the single module 11 or a sparse distribution of modules 11 connects with a gantry of a SPECT system. The module 11 is placed adjacent to the gamma camera, so the gantry of the gamma camera moves the module 11. Alternatively, a collimator may be positioned between the modules 11 and the patient or between the scatter and catcher detectors 12, 13, allowing the scatter and/or catcher detectors 12, 13 of the modules 11 to be used for photoelectric event detection for SPECT imaging instead of or in addition to detection of Compton events.

The module-based segmentation of the Compton sensor allows the same design of modules 11 to be used in any different configurations. Thus, a different number of modules 11, module position, and/or configuration of modules 11 may be used for different medical imaging systems. For example, one arrangement is provided for use with one type of CT system and a different arrangement (e.g., number and/or position of modules 11) is used for a different type of CT system.

The module-based segmentation of the Compton sensor allows for more efficient and costly servicing. Rather than replacing an entire Compton sensor, any module 11 may be disconnected and fixed or replaced. The modules 11 are individually connectable and disconnectable from each other and/or the gantry 50. Any bridges are removed, and then the module 11 is removed from the medical imaging system while the other modules 11 remain. It is cheaper to replace an individual module 11. The amount of time to service may be reduced. Individual components of a defective module 11 may be easily replaced, such as replacing a scatter or catcher detector 12, 13 while leaving the other. The modules 11 may be configured for operation with different radioisotopes (i.e., different energies) by using corresponding detectors 12, 13.

Figure 10:
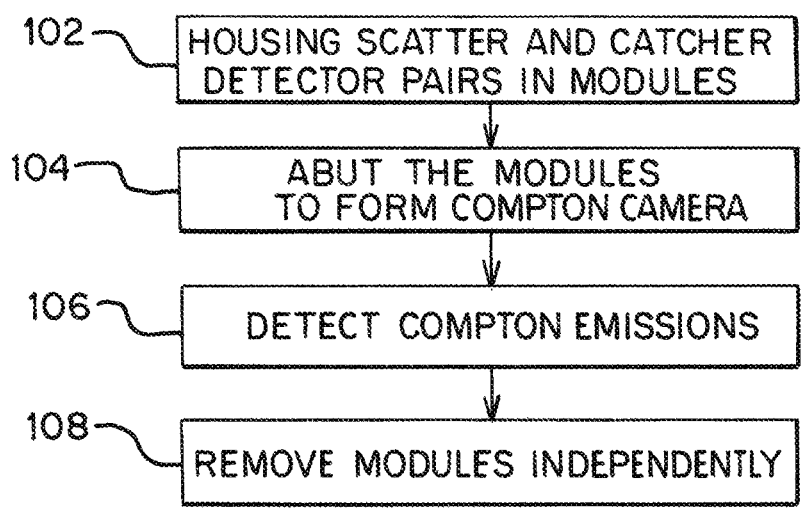
FIG. 10 is a flow chart diagram of an example embodiment of a method for forming a Compton camera.

FIG. 10 shows one embodiment of a flow chart of a method for forming, using, and repairing a Compton camera. The Compton camera is formed in a segmented approach. Rather than hand assembling the entire camera in place, scatter detector and catcher detector pairs are positioned relative to each other to form a desired configuration of the Compton camera. This segmented approach may allow different configurations using the same parts, ease of assembly, ease of repair, and/or integration with other imaging modalities.

Figure 11:
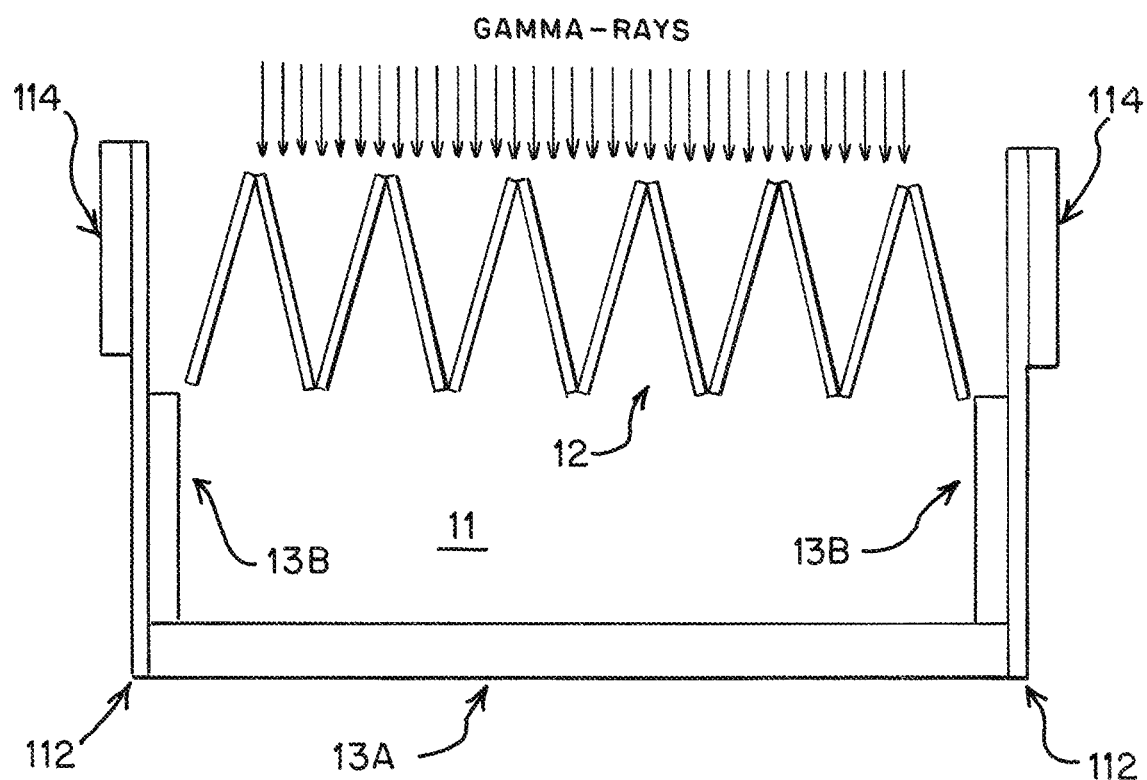
FIG. 11 illustrates one embodiment of a module with a tilted scatter detector and a near $2\pi$ catcher detector.

Other embodiments form a combination of a Compton camera and a SPECT camera. The segmented modules 11 of FIG. 11 are used. The modules of FIGS. 13-16 may be used for forming a SPECT camera. The detector arrangement of FIG. 11 may be used.

The method may be implemented by the system of FIG. 1 to assemble a Compton sensor as shown in any of FIGS. 4-9. The method may be implemented by the system of FIG. 11 to assemble a Compton sensor as shown in any of FIGS. 13-16. Other systems, modules, and/or configured Compton sensors may be used.

The acts are performed in the order shown (i.e., top to bottom or numerically) or other orders. For example, act 108 may be performed as part of act 104.

Additional, different, or fewer acts may be provided. For example, acts 102 and 104 are provided for assembling the Compton camera without performing acts 106 and 108. As another example, act 106 is performed without other acts.

In act 102, scatter and catcher detector pairs are housed in separate housings. Modules are assembled where each module includes both a scatter detector and a catcher detector. A machine and/or person manufactures the housings.

The modules are shaped to abut where the scatter and catcher detector pairs of different ones of the housings are non-planar. For example, a wedge shape and/or positioning is provided so that the detector pairs from an arc, such as shown in FIG. 4C. The shape allows and/or forces the arc shape when the modules are positioned against one another.

In act 104, the housings are abutted. A person or machine assembles the Compton sensor from the housings. By stacking the housings adjacent to each other with direct contact or contact through spacers, gantry, or framework, the abutted housings form the arc. A full ring or partial ring is formed around and at least in part defines a patient space. Based on the design of the Compton camera or Compton-SPECT camera, any number of housings with the corresponding scatter and catcher detector pairs are positioned together to form a camera.

The housings may be abutted as part of a multi-modality system or to create a single imaging system. For a multi-modality system, the housings are positioned in a same outer housing and/or relative to a same bed as the sensors for the other modality, such as SPECT, PET, CT, or MR imaging system. The same or different gantry or support framework may be used for the housings of the Compton camera and the sensors for the other modality. For other embodiments, the modules provide the multi-modality by providing for both a Compton camera and the SPECT imaging system.

The configuration or design of the Compton camera defines the number and/or position of the housings. Once abutted, the housings may be connected for communications, such as through one or more bridges. The housings may be connected with other components, such as an air cooling system and/or a Compton processor.

In act 106, the assembled Compton camera detects emissions. A given emitted photon interacts with the scatter detector. The result is scattering of another photon at a particular angle from the line of incidence of the emitted photon. This secondary photon has a lesser energy. The secondary photon is detected by the catcher detector. Based on the energy and timing of both the detected scatter event and catcher event, the events are paired. The positions and energies for the paired events provides a line between the detectors and an angle of scattering. As a result, the line of incidence (e.g., Compton cone of incidence) of the emitted photon is determined.

To increase the likelihood of detecting the secondary photon, the catcher events from one housing may be paired with the scatter events of another housing. Due to the angles, scatter from one scatter detector may be incident on the paired catcher detector in the same housing or a catcher detector in another housing. By the housings being open in the detector region and/or using low photon attenuating materials, a greater number of Compton events may be detected.

The detected events are counted or collected. The lines of response or lines along which the different Compton events occur are used in reconstruction. The distribution in three dimensions of the emissions from the patient may be reconstructed based on the Compton sensing. The reconstruction does not need a collimator as the Compton sensing accounts for or provides the angle in incidence of the emitted photon.

The detected events are used to reconstruct the locations of the radioisotope. Compton and/or photoelectric images are generated from the detected events and corresponding line information from the events.

In act 108, a person or machine (e.g., robot) removes one of the housings. When one of the detectors or associated electronics of a housing fails or is to be replaced for detecting at different energies, the housing may be removed. The other housings are left in the medical imaging system. This allows for easier repair and/or replacement of the housing and/or detectors without the cost of a greater disassembly and/or replacement of the entire Compton camera.

FIGS. 11-15 are directed to a Compton camera with a tilted scatter detector and/or a near $2\pi$ catcher detector. Using the modules of FIGS. 1-9 or another Compton camera, the scatter and/or catcher layers are arranged to capture a greater percentage of emissions from a patient and/or scatter. The scatter layer is configured in a tilted configuration. The catcher layer is formed as a near $2\pi$ catcher layer. Collimation may be used between modules to exclude large Compton angle events, which degrade image quality, thus improving signal-to-noise in the image and reducing demands on the ASIC/FPGA.

FIG. 11 shows one embodiment of a module 11 of a Compton camera for a medical imaging system. A tilted scatter layer and a near $2\pi$ catcher layer are provided. The tilted scatter layer results in a greater volume for scattering. The near $2\pi$ catcher detector results in greater opportunity to catch scattered photons by catching scatter over a wider range of angles.

The module 11 may be the entire Compton camera or multiple such modules 11 form the Compton camera. The module 11 of the medical imaging system includes a tilted scatter layer of scatter detectors 12, a bottom catcher detector 13A, and side catcher detectors 13B, inter-module shielding 112 to reduce cross-talk, and inter-module slits and/or slats (i.e., collimator) 114 to block large scatter Compton angle events and reduce the load on the ASICs or FPGAs of the detectors 12, 13. Additional, different, or fewer components may be provided. For example, the tilted scatter detector 12 is provided without the near $2\pi$ catcher detectors 13A, 13B or vise versa. As another example, the shielding 112 and/or slits or slats 114 are not provided. In another example, the ASICs or FPGAS, circuit boards, housing, or other components are provided.

The dimensions in the drawing are arbitrary and sized for explanation. Other relative sizes may be used. Since FIG. 11 is a cross-section, other components may be provided in front or beyond FIG. 11. For example, side wall catcher detectors 13B, shielding 112, and/or slits or slats 114 are provided on side walls in parallel with the plane of the drawing sheet. In other embodiments, one or more of the side walls does not include side wall catcher detectors 13B, shielding 112, and/or slits or slats 114.

The module 11 is positioned relative to a patient space, bore of the medical imaging system, and/or bed 60 as discussed above for FIGS. 5-9 or another configuration. The patient bed 60 supports the patient in the patient space. The bed 60 may be moveable, such as a robot or roller system for moving the patient into and out of the medical imaging system. The outer housing of the medical imaging system and/or scatter layer create a bore into which the patient bed 60 is positioned. The bore defines the patient space for imaging the patient. The bore may be of any dimension in a cross-sectional plane orthogonal to a longitudinal or iso center axis, such as 70 cm. The center of the bore along a longitudinal axis of the cylindrical shaped bore or center of the patient space is the iso center axis. The bed 60 moves along the iso center axis.

The scatter detector 12 is arranged to receive emissions from a patient. In FIG. 11, gamma rays are shown in parallel directed to a front face of the scatter detector 12. The gamma rays emitted from the patient are not all parallel, so may arrive at the front face at any of various angles. The module 11 is positioned so that gamma rays directed to the module 11 are likely to intersect the scatter detector 12 before the catcher detector 13. The scatter detector 12 has an outer surface facing the iso center axis.

For tilting, the outer surface is away from orthogonal by an angle of at least 10-80 degrees (e.g., at least 20, 30 or 45 degrees) to a radial line extending perpendicular from the iso center axis through a center or other part of the scatter detector 12. Any angle may be used, such as being 35, 45, 65, or 75 degrees. Where the scatter detector 12 is a plate orthogonal to the radial line, a given area may fit in the module 11. By tilting, the outer surface facing the patient may have a greater area. This results in a greater likelihood of scatter as the volume for interaction is greater. Greater angles result in greater area of the face and volume of the detector 12, resulting in greater likelihood of scatter for any given photon.

The tilt is with respect to the radial from perpendicular to the iso center axis. No tilt corresponds to the scatter detector 12 being a plate orthogonal to a radial, which is perpendicular to the iso center axis. The tilt may be relative to the front or back surface of the module 11 or the back or rear wall catcher detector 13A.

The absolute number of scattered photons is increased by: a) using scatter layer detector materials that favor Compton scatter vs. photoelectric effect (low-Z materials where low Z is 30 or less); b) adding more scatter material in the scatter layer; and c) maximizing the number of scattered events that contribute to have a better overall image quality by eliminating, using physical or digital collimation, Compton events that have large Compton angle uncertainties. By increasing the number of scattered photons escaping from the scatter layers and reaching the catcher layer (tilting), the probability that Compton events escape from the scatter layer is increased by reducing the mean-free path of those events at the scatter layer. The increase in scatter increases the number of scattered photons reaching the catcher layer. Fewer scatter detector modules (per absolute number of scatter events reaching the catcher layer) may be used due to a larger escape probability using tilted geometry. The tilting results in a larger number of pixels in projection orthogonal to the radial in the scatter detector 12, increasing resolution.

In the embodiment shown in FIG. 11, the scatter detector 12 is formed from a plurality of plates positioned in an accordion arrangement. To increase the number of scatter events, the plates of the scatter detector 12 are configured in a tilted configuration with no gaps between detector plates. The plates are abutted to create the accordion arrangement. Gaps are provided in other embodiments. The plates tilt in a repeating sequence of two angles. Other arrangements with sequences of three or more plates and three or more corresponding angles may be used. In alternative embodiments, the scatter detector is a single plate that is tilted. In yet other embodiments, one or more plates of the detectors are orthogonal to the radial (e.g., parallel with the rear wall catcher detector 13A) while other plates are tilted. Alternatively, the plates do not abut, but instead are all tilted at the same angle and in parallel to each other (see FIG. 15).

Using plates and the accordion arrangement, the same arrangement extends between side walls into and out of the plane of the drawing. In other embodiments, the scatter detector 12 varies in angle or tilting into and out of the plane of the drawing as well as through the cross section of the drawing. Any 3D surface that is non-planar may be used.

The tilting maximizes the absolute number of scattered photons for the scatter layer, thus increasing the absolute number of scattered photons reaching the catcher layer. Since scattering is more likely to occur due to the tilting, a larger variety of detector materials may be used, such as Si, HPGe, CdTe, CZT, GaAs, TlBr and others, due to inherent easiness of fabrication of more uniform detectors with thinner thickness. The tilt counteracts some of the loss of scatter volume in a thinner detector. Fewer scatter detector modules are required per absolute number of scatter events reaching the catcher due to a larger escape probability using tilted geometry. Due to the tilting, there is a greater pixel density of the scatter detector relative to viewing from the iso center axis. Position resolution improves using the tilted geometry due to a larger number of pixels (ASIC channels) per unit of projected area along the radials.

The catcher detector 13 is positioned behind the scatter detector 12 relative to the patient space. The catcher detector 13 is spaced from the scatter detector 12, forming a volume between the detectors 12, 13. One or more parts of the catcher detector 13 may contact one or more parts of the scatter detector 12, such as at the sides of the module 11. Gaps may be provided between the scatter detector 12 and the catcher detector 13 with no contact. The catcher detector 13 may extend to be at a same z-depth as part of the scatter detector 12, such as due to the tilt of the scatter detector 12 and/or due to the surround shape of the catcher detector 13.

The catcher detector 13 forms a substantially semi-spherical surround behind the scatter detector 12 relative to the patient space. Substantially is used to account for gaps at joints, one or two of four sides not including a side wall catcher detector 13B, the side wall catcher detectors 13B starting at a z-depth (i.e., along the radial perpendicular to the iso center axis) that is 30 degrees or less from a plane orthogonal to the radial at a depth of the deepest part of the scatter detector 12, and/or the side wall catcher detectors 13B starting at a z-depth (i.e., along the radial perpendicular to the iso center axis) that is 10 cm or less deeper than the plane orthogonal to the radial at a depth of the deepest part of the scatter detector 12. A multi-sided detector front surface is provided. The catcher detector 13 is non-planar. A front face or surface through which the scattered photons enter the detector 13 is non-planar. The catcher detector 13 is formed in a cup, box, or semi-sphere of three or more sides to at least partially (i.e. substantially) surround a volume behind the scatter detector 12. This provides a near $2\pi$ structure behind the scatter detector 12 relative to the patient.

In one embodiment, the substantially semi-spherical surround is formed from a plurality of planar plates, such as the rear wall catcher detector 13A and two or more side wall catcher detectors 13B (e.g., the rear wall catcher detector 13A and four side wall catcher detectors 13B forming a cuboid of five sides with one open side directed to the scatter detector 12). The plates are at right angles to each other, but greater or lesser angles may be provided. The plates are substrates positioned in non-parallel planes within the module 11. Semiconductor or other processes for forming the detectors as slabs may be used to form the plates, which are then positioned in the module 11 to provide the substantially semi-spherical surround. Four-sided square or rectangular plates are used in FIG. 11, but three, five, six, or other numbers of sides may be used.

The catcher layer geometry at least partly surrounds the space behind the scatter layer, such a providing a near $2\pi$ solid angle geometry. This surround may result in catching more scatter photons. For example, near 100% scattered/caught ratio may be achieved by adding catcher layers in-between modules (i.e., the side wall catcher detectors 13B). A larger field of view of the Compton-camera in the Z-direction (bed direction) is provided. The absolute number of scattered/caught fraction of photons is increased by: a) increasing the solid angle between the scatter layer and the catcher layer; b) increasing the area of the catcher layer; c) reducing the distance between scatter and catcher layers; d) increasing the effective thickness of the catcher layer; e) and/or selecting materials favoring photoelectric effect vs. Compton scatter in the catcher layer. By shaping the catcher detector 13 as multi-sided in a surround of the volume behind the scatter detector 12, the solid angle is increased, the area of the front face of the catcher detector is increased, the distance between the scatter detector 12 and the catcher detector 13 may be decreased, and the effective thickness of the catcher layer is increased.

The shields 112 are shielding material, such as lead or tungsten. The shields 112 are gamma ray shields. Materials and thickness that are opaque to a given percentage (e.g., 75-100%) of the emissions at the isotope energies are positioned at the side walls (e.g., covering part or the entire wall) or are the side walls of the module 11. The shielding material is provided over the entire side wall, such as adjacent ends and over the z-axis extent (i.e., depth along the radial) of the scatter detector 12 and the catcher detector 13. In other embodiments, the shielding material has a lesser extent, such as beginning on the side walls at a deepest extent of the scatter detector 12 to the catcher detector 13 or to a deepest part of the catcher detector 13.

The shields 112 may be on all walls but a side of the module 11 facing the patient space. Alternatively, one or more side walls and/or the rear wall do not include the shields 112. Where multiple modules 11 abut each other, one shield 112 between them may be provided rather than having abutting shields 112 from the two modules 11. The shielding material separates the modules 11. Inter-module cross-talk is reduced by adding inter-module shielding.

The slits and/or slats 114 are collimators formed from plates. The plates are positioned in parallel to each other, forming slits through which photons may pass. In other embodiments, the slits and/or slats 114 are collimators with holes at a desired angle. Any size holes may be used.

The slits and/or slats 114 are angled to allow photons at some angles to pass and absorbing or blocking photons at other angles. For example, the slits and/or slats 114 are angled to absorb large angle scattered photons (e.g., 80-110 degrees from the radial). The large angle scattered photons contain large angular uncertainty and may be noise for adjacent modules. The slits and/or slats 114 may improve image quality and reduce ASIC or FPGA 122 requirements by reducing noise-related photons.

The slits and/or slats 114 are provided adjacent to the scatter detector 12, such as with a same depth extent on two or more side walls of the module 11. Other extents or positioning may be provided. The slits and/or slats 114 may be part of the module 11 or positioned between modules 11.

Figure 12A:
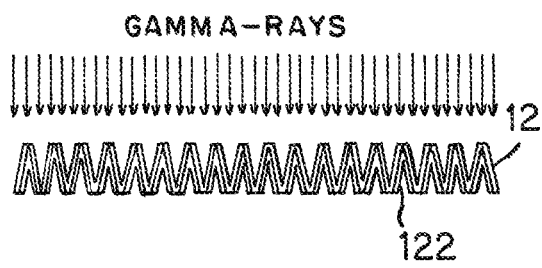
FIG. 12A illustrates one embodiments of a titled scatter detector with parallel application specific integrated circuits.

The scatter detector 12 includes application specific integrated circuits (ASIC) or field programmable gate arrays (FPGA) for reading the scatter detector 12. A separate ASIC or FPGA is provided for each group of pixels in the scatter detector 12. The ASIC or FPGA is formed as part of the substrate with the scatter detector 12 or may be formed separately. The ASIC or FPGA 122 is positioned in parallel with the scatter detector 12 as shown in FIG. 12A. In this position, some scatter photons are caught in the ASIC or FPGA 122, resulting in loss of the Compton event.

Figure 12B:
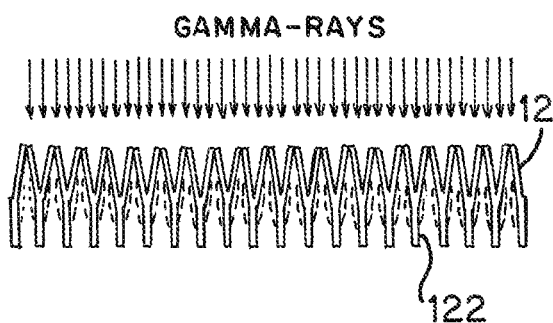
FIG. 12B illustrates the tilted scatter detector with the application specific integrated circuits in a non-parallel arrangement.

FIG. 12B shows another embodiment. The ASICs or FPGAs 122 electrically connect to the scatter detector 12 by traces on flexible circuit material or by wires. The ASICs or FPGAs 122 are positioned in parallel with the radial lines from the iso center axis, minimizing the area of interaction with scatter. The ASICs or FPGAs 122 are plates or substrate positioned to be non-parallel with the outer or front facing surface of the scatter detector 12. In other embodiments, the ASICs or FPGAs 122 of the scatter detector 12 are removed from the field of view, such as being behind the catcher detector 13 relative to the patient. The ASICs or FPGAs 122 are positioned to reduce the effect on Compton kinematics.

FIG. 11 shows one module 11. The Compton camera is formed from the single module 11 or from multiple modules 11. Each module 11 includes the tilted scatter detector 12 and/or near $2\pi$ catcher detector 13. The modules 11 may have housing shapes to stack or abut for forming a ring or partial ring, such as having the wedge shape of FIG. 1. Other shapes may be used.

For a multi-module Compton camera, the scatter layer is formed from a plurality of scatter detectors 12, such as using the modular system of FIGS. 1-9. Similarly, the catcher layer 13 is formed from a plurality of catcher detectors 13. For example, eighteen modules 11 provide for eighteen pairs of scatter and catcher detectors 12, 13. More or fewer modules 11 may be used. The modules 11 may have any arrangement, such as one or more axially spaced rings and/or partial rings or one or more sparsely distributed modules 11 or groups of modules. The modules 11 may be part of a multi-modality imaging system or for a Compton-camera only system. The scatter and catcher detectors 12, 13 (e.g., modules 11) are positioned to receive emissions from a patient on the patient bed 60 or otherwise in the patient space.

The module 11 may be positioned adjacent to none, one, two, three, or four other modules 11. Where the scatter detector 12 is tilted with a repeating pattern along one dimension, the modules 11 may be abutted or positioned adjacent to each other along two sides. Where the scatter detector 12 is tilted with a repeating pattern along two dimensions, the modules 11 may be abutted or positioned adjacent to each other along four sides. In other embodiments, the module 11 may abut along 1-4 sides regardless of the tilt arrangement.

Figure 13A:
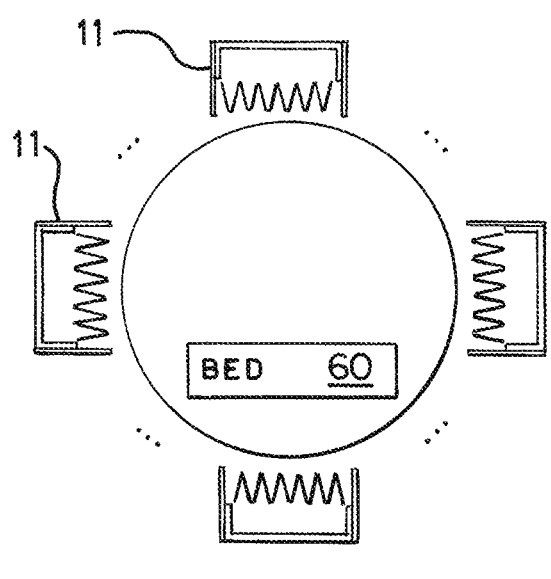
FIGS. 13A and B show orthogonal cross-sections of a multi-ring configuration of modules in a Compton camera according to a first embodiment.
Figure 13B:
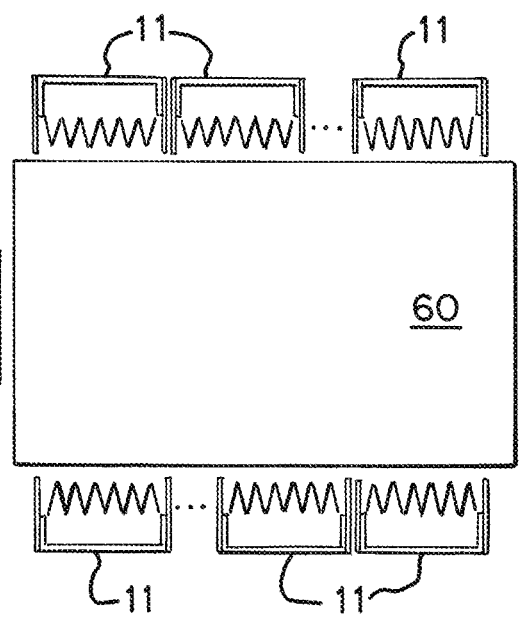

In one embodiment, the modules 11 are positioned to form one or more axially spaced partial or full rings. FIGS. 13A and 13B show at least three full or partial rings around the patient space and the patient bed 60. Additional or fewer rings and/or partial rings may be provided. FIG. 13A is a view of a cross section orthogonal to the iso center axis at one of the rings or partial rings. FIG. 13B is cross-section view of a plane parallel with the bed 60 and along the iso center axis.

The near $2\pi$ catcher detectors 13 of the modules include side wall catcher detectors 13B positioned on sides abutting modules 11 in the same ring and modules 11 of other rings. Each module 11 operates independently so that scatter from one module 11 is not paired with capture in the catcher detector 13 of another module 11. Timing, power, or other information may be or may not be shared between modules. Since the modules 11 are fully isolated modules, the modules 11 may stack or abut on any of four sides.

Figure 14A:
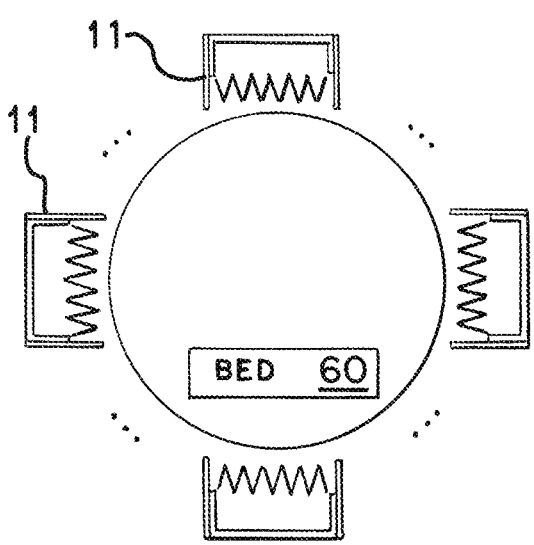
FIGS. 14A and B show orthogonal cross-sections of a multi-ring configuration of modules in a Compton camera according to a second embodiment.
Figure 14B:
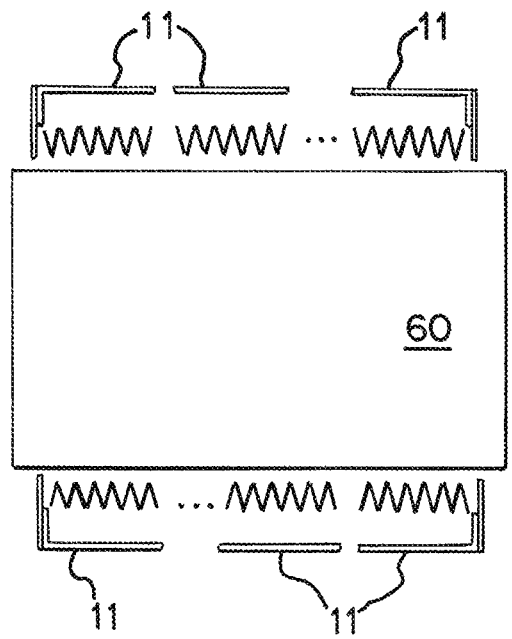

In alternative embodiments, Compton events may be formed from scatter from one module 11 and capture of the scatter photon in another module 11. FIGS. 14A and 14B show cross sections where the side wall catcher detectors 13B for the sides adjacent to other rings or partial rings are removed or not provided. The modules 11 within a given ring or partial ring are isolated from each other. The adjacent modules 11 across rings share a common synchronization and/or clock for event detection by the ASICs or FPGAs of the detectors 12, 13, allowing a Compton pair of events using scatter in one module 11 and capture of the scatter photon in another module 11. The surround of the catcher detectors 13 in the modules of the axially outer rings or partial rings have side wall catcher detectors 13B on three sides. The surround of the catcher detectors 13 in the axially inner rings or partial rings have side wall catcher detectors 13B on two sides (sides adjacent modules 11 in the same ring or partial ring). In alternative embodiments, modules are not isolated within a ring or partial ring but are isolated between rings or partial rings. In yet other embodiments, one or more modules 11 may not be isolated within a ring and between rings. The near 2π catcher layer is formed from the catcher detectors 13 of multiple modules 11.

Figure 15:
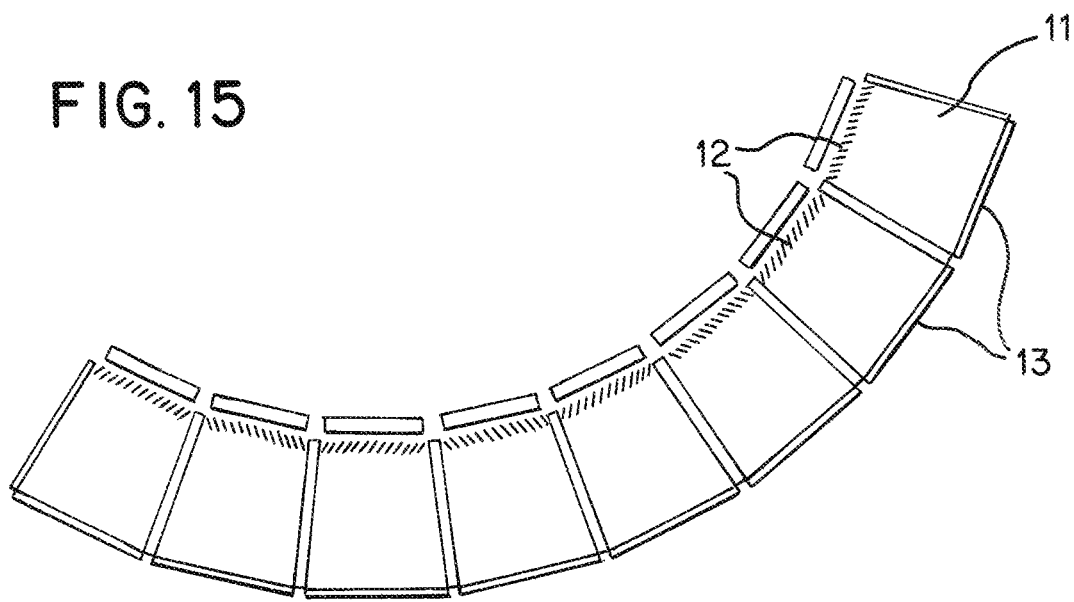
FIG. 15 illustrates different tilting of scatter detectors in different modules according to one embodiment.

FIG. 15 shows a partial ring of modules 11. The modules 11 have wedge shapes for closer stacking. FIGS. 13 and 14 show cube shapes where gaps are provided at least further from the iso center axis when the modules 11 are stacked adjacent each other in the ring or partial ring.

In FIG. 15, the scatter detectors 12 are tilted. The plates of detectors forming the tilted scatter detector 12 are arranged in parallel planes. All the plates of a scatter detector 12 in a module 11 tilt in the same direction or towards a given side. Within the ring or partial ring, the scatter detectors 12 of the different modules 11 tilt the same direction or in different directions. Different patterns or tilt structures may be provided between different modules 11 or by groups of modules 11, such as the every-other pattern of opposite tilting between adjacent modules 11 of FIG. 15. Any grouping of tilt pattern across modules 11 and/or within modules 11 may be used.

The pattern or grouping may correspond to isolation or cross-talk between modules 11. For example, pairs of modules 11 with opposite tilt of the scatter detector 12 share a synchronization signal and/or clock but are isolated from other pairs. The side wall catcher detectors 13B between modules 11 sharing the synchronization signal and/or clock (i.e., with cross talk) are not provided. The side wall catcher detectors 13B between modules 11 not grouped are provided. In other embodiments, the paired or grouped modules 11 for cross talk have a same tilt as each other. The tilt for other groups is the same and/or different.

The Compton processor 19 (e.g., image processor) is configured to generate a Compton image from Compton events detected from the tilted scatter and near 2π catcher detectors 12, 13. The electronics of the modules 11 or other electronics output events detected from the detectors 12, 13. The location, energy, and time of the events are received by the Compton processor 19. These events are paired using the location, energy, and/or time. Based on the pairing, location, and energy, an angle of incidence of the emission from the patient onto the scatter detector 12 is determined. The angle may be expressed probabilistically, such as a cone of incidence. Using reconstruction from many detected Compton events and the angles of incidence, a spatial distribution in patient or object space of the emissions is determined. A Compton image is rendered from the spatial distribution.

The display 22 displays the Compton image. Other images may be displayed with the Compton image. The tilted scatter detector 12 and/or near 2π catcher detector 13 result in a greater number of Compton events being captured, so the resulting Compton image has more information. This better image quality results in a diagnostically improved image.

The Compton processor 19 is configured to perform digital collimation. Once events are paired, the angle of the scatter from the scatter detector 12 for a given event is determined. The relationship of energy and angle and the positions of the paired events indicates the angle of the scatter photon. Compton events may be rejected based on the angle, such as applying one or more scatter angle thresholds. The Compton image is generated from the Compton events that are not rejected. In other embodiments, digital collimation is not used.

Figure 16A:
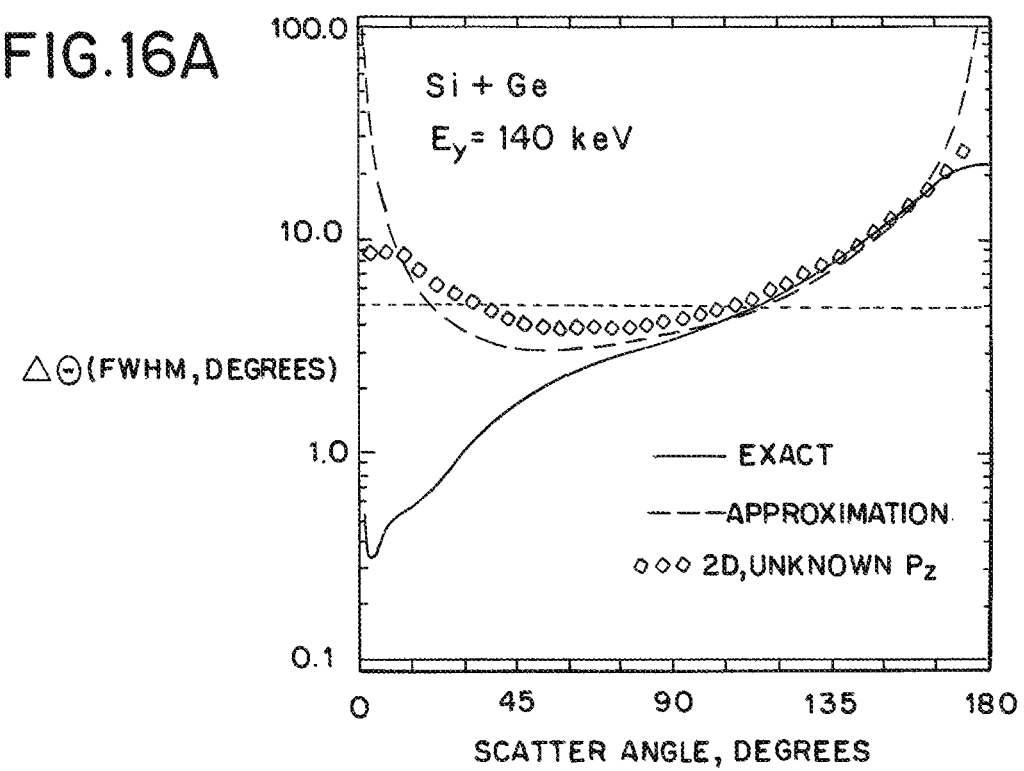
FIG. 16A shows an example graph of full width, half maximum (FWHM) by scatter angle for Compton imaging.
Figure 16B:
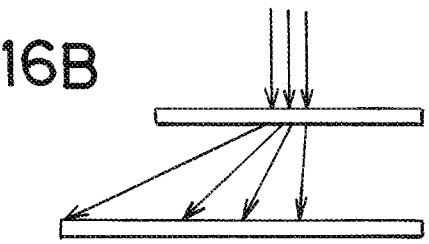
FIG. 16B shows example scatter angles.

FIG. 16A shows angular uncertainties in the Compton angle as a function of Compton angle. Compton events with some scatter angles may result in worse image quality. For example, the FWHM of a back projected cone is to be at a desired level, such as represented by the horizontal dashed line. The FWHM for a given Compton event is above or below the desired FWHM based on the scatter angle. For example, angles between 40 degrees and 120 degrees provide information with sufficient FWHM. FIG. 16B shows different scatter angles given emissions orthogonal to the scatter detector. Compton events for lesser (e.g., less than 40 degrees) and/or greater (e.g., greater than 120 degrees) scatter angles are not used (i.e., rejected by digital collimation). The remaining Compton events are used to generate the Compton image.

In one example, a CZT scatter detector 12 and CZT catcher detector 13 have a 30 cm distance between scatter and catcher layers with a 70 cm bore diameter. A PSF with FWHM <40.0 mm is produced by rejecting events with Compton angle greater than ~40°. Other thresholds may be used.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A Compton camera for medical imaging, the Compton camera comprising:
    a bed for a patient space having an iso center axis;
    a first module having a first scatter detector and a first catcher detector spaced from the first scatter detector, the first scatter detector formed from a plurality of plates positioned back and forth in an accordion arrangement, wherein each of the plates of the plurality of plates include an outer surface facing the iso center axis where the outer surface is tilted away from orthogonal by an angle of at least 20 degrees to a radial line extending perpendicular from the iso center axis through a center of the first scatter detector, the first catcher detector forming a substantially semi-spherical surround behind the first scatter detector relative to the patient space;
    an image processor configured to determine angles of incidence for Compton events from the first scatter detector and the first catcher detector.

2. The Compton camera of claim 1 wherein the angle is at least 45 degrees to the radial line extending perpendicular from the iso center axis through the center of the first scatter detector.

3. The Compton camera of claim 1 wherein the first scatter detector comprises a tilted arrangement relative to the radial line.

4. The Compton camera of claim 1 wherein the substantially semi-spherical surround comprises a five-sided cuboid with an open side adjacent to the first scatter detector.

5. The Compton camera of claim 1 wherein the substantially semi-spherical surround comprises a plurality of planar catcher substrates positioned on non-parallel planes within the first module.

6. The Compton camera of claim 1 further comprising application specific integrated circuits or field programmable gate arrays for reading the first scatter detector, the application specific integrated circuits or field programmable gate arrays forming plates positioned to be non-parallel with the outer surface.

7. The Compton camera of claim 1 further comprising shielding material on sidewalls of the first module.

8. The Compton camera of claim 7 further comprising a second module having a second scatter detector and a second catcher detector spaced from the second scatter detector, the shielding material separating the first module from the second module.

9. The Compton camera of claim 1 further comprising a second module having a second scatter detector and a second catcher detector spaced from the second scatter detector, the surround including the second catcher detector.

10. The Compton camera of claim 1 further comprising additional modules having additional scatter detectors and additional catcher detectors spaced from the additional scatter detectors, the first module and additional modules forming a ring or partial ring around the patient space.

11. The Compton camera of claim 1 wherein the image processor is configured to generate a Compton image from the Compton events and the angles of incidence, and further comprising a display configured to display the Compton image.

12. A medical imaging system comprising:
a Compton camera comprising a scatter detector arranged to receive emissions from a patient, the scatter detector formed from a plurality of plates positioned back and forth in an accordion arrangement, wherein each plate of the plurality of plates includes an outer surface facing the patient where the outer surface is away from orthogonal by an angle of at least 20 degrees to a radial line extending perpendicular from a longitudinal axis of the patient through the scatter detector.

13. The medical imaging system of claim 12 wherein the Compton camera further comprises a near a structure behind the scatter detector relative to the patient.

14. The medical imaging system of claim 12 wherein the scatter detector is in a module, and further comprising gamma ray shielding material on a side of the module.

15. A medical imaging system comprising:
a Compton camera comprising a scatter detector and a catcher detector, the scatter detector arranged to receive emissions from a patient, the catcher detector arranged to receive scatter from the scatter detector due to the emissions from a patient, the catcher detector comprising a multi-sided detection surface positioned behind the scatter detector relative to the patient, wherein the scatter detector is formed from a plurality of plates positioned back and forth in an accordion arrangement, wherein each plate of the plurality of plates includes an outer surface facing the patient where the outer surface is away from orthogonal by an angle of at least 20 degrees to a radial line extending perpendicular from a longitudinal axis of the patient through the scatter detector.

16. The medical imaging system of claim 15 wherein the multi-sided detection surface comprises a near $2\pi$ a structure.

17. The medical imaging system of claim 15 wherein the scatter detector and catcher detector are in a module, and further comprising gamma ray shielding material on a side of the module.

* * * * *